Figure 1:
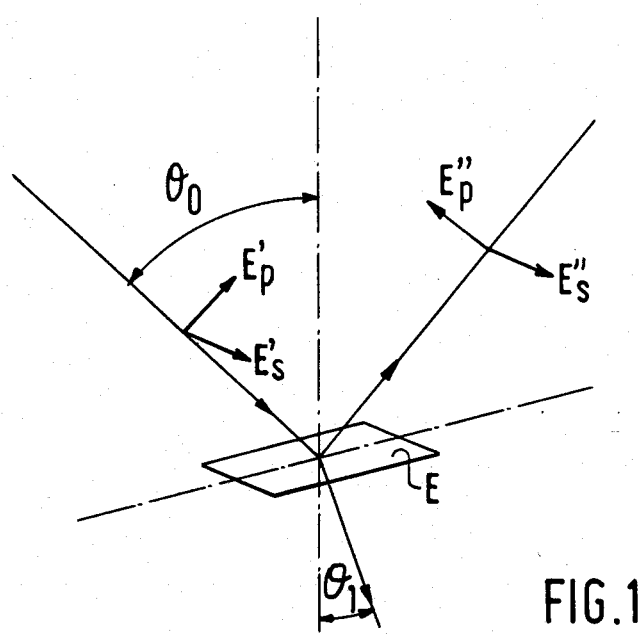

United States Patent [19]

Erman et al.

[11] Patent Number: 4,790,659

[45] Date of Patent: Dec. 13, 1988

[54] OPTICAL SAMPLE ILLUMINATION DEVICE FOR A SPECTROSCOPIC ELLIPSOMETER HAVING A HIGH LATERAL RESOLUTION

[75] Inventors: Marko Erman, Paris; Claude E. Hily, Ozouer-Le-Voulgis; Jean Le Bris, Quincy Sous Senart, all of France

[73] Assignee: U.S. Philips Corporation, New York, N.Y.

[21] Appl. No.: 108,510

[22] Filed: Oct. 13, 1987

[30] Foreign Application Priority Data

Oct. 10, 1986 [FR] France ................. 86 14123

[51] Int. Cl.$^4$ .......................................... G01N 21/21
[52] U.S. Cl. .................................. 356/369; 356/327
[58] Field of Search ............... 356/327, 331, 332, 369

[56] References Cited

PUBLICATIONS

Theeten et al., "In Situ Measurement and Analysis of Plasma-Grown GaAs Oxides with Spectroscopic Ellipsometry", *J. Electrochem. Soc.: Solid-State Sci. & Tech.* pp. 378–385, 2/80.

Primary Examiner—Davis L. Willis
Assistant Examiner—Matthew W. Koren
Attorney, Agent, or Firm—Paul R. Miller

[57] ABSTRACT

The invention relates to an optical sample illumination device for a spectroscopic ellipsometer of the rotating analyzer type. The image of the exit slit (F') of a monochromator is conjugated with a point (F'$_2$) of a surface of a sample (E) by means of two spherical mirrors (M$_7$ and M$_8$). An astigmatism correction slit (F'$_{1S}$) is arranged in the proximity of the conjugate (F'$_1$) of the exit slit(F') of the monochromator with respect to the spherical mirror (M$_7$) and is arranged perpendicularly to this exit slit and to the optical path so that said correction slit is conjugated with the said point (F'$_2$) through the spherical mirror (M$_8$). A luminous spot without astigmatic errors is thus obtained.

2 Claims, 3 Drawing Sheets

OPTICAL SAMPLE ILLUMINATION DEVICE FOR A SPECTROSCOPIC ELLIPSOMETER HAVING A HIGH LATERAL RESOLUTION

The invention relates to an optical sample illumination device for a spectroscopic ellipsometer of the rotating analyzer type, comprising a monochromator having an exit slit whose image is conjugated with a surface of the sample by at least a first spherical mirror, and comprising a polarizer arranged between said spherical mirror and the sample.

Such a device which is known from the Article "High Precision Scanning Ellipsometer" by D. E. ASPNES et al. published in the magazine Applied Optics in January 1975 is suitable for carrying out the conventional ellipsometry which operates with plane waves and a high sensitivity to the surface condition of the sample but with a low lateral resolution.

In the above-mentioned Article the angular aperture of the beam illuminating the sample does not exceed 1°. This low value permits of considering the measurement as being made by means of plane waves.

The Article "Geometrical Resolution in the Comparison Ellipsometer" by STIBLERT et al. published in the Journal de Physique (Symposium C10, supplement to no. 12, volume 44, December 1983) describes a comparison ellipsometer having a good sensitivity to the surface condition and a high lateral resolution of the order of 2 microns corresponding to the dimension of the spot illuminating the sample with convergent light. If the sensitivity to the surface condition is given by the presence of plane waves having a defined state of polarization, the lateral resolution can in itself only be obtained by an optical focussing system which is contradictory to the concepts of both plane wave and a single angle of incidence. In the afore-mentioned Article the lateral resolution of the order of 2 microns is obtained at the expense of a less satisfactory depth resolution.

The analysis of perturbations of the measurements due to the use of convergent rays has led the Applicant to calculate a compomise resulting in the conception of an ellipsometer of the rotating analyzer type having a satisfactory precision for the two aforementioned parameters. This compromise is a choice of a lateral resolution of the order of 10×10 microns with an angular aperture of the incident beam of the order of 4 to 5 degrees which permits of maintaining a sensitivity to the surface condition which is better than 1 Ångström.

For such values of the angular aperture the wave can no longer be considered as being plane and the interpretation of results necessitates a new form of calculation.

In the conventional ellipsometry the ratio of complex reflectance $\rho$ is measured as follows:

$$\rho = R_p R_s^{-1} = \tan \Psi \exp(i\Delta) \qquad (1)$$

in which $R_p$ and $R_s$ denote the reflection coefficients of the linearly polarized waves having their polarization parallel and perpendicular, respectively, to the plane of incidence.

An ellipsometer of the rotating analyzer type permits of directly measuring $\tan \Psi$ and $\cos \Delta$:

$$\tan \psi = \left|\left|\frac{R_p}{R_s}\right|\right| \qquad (2)$$

-continued $$\cos \Delta = \frac{R_e(R_p \cdot R_s)}{||(R_p \cdot R_s)||} \qquad (3)$$

in which $R_e$ is the real part of a complex number.

In the case of a non-plane wave allowance must be made for the fact that the coefficients $R_p$ and $R_s$ are dependent on the angle of incidence $\theta$. The luminous incident beam is broken up into a sum of plane waves and the Fourier transform of its distribution is designated by g and that of the reflected and collected beam is designated by g'.

Thus the following formula is obtained for coherent light and for a homogeneous sample, in which formula the sign * designates a convolution product:

$$\tan \psi = \frac{||[R_p(\theta)^* g \cdot g'(\theta)](\theta_o)||}{||[R_s(\theta)^* g \cdot g'(\theta)](\theta_o)||} \qquad (4)$$

in which $\theta_o$ = average angle of incidence and $$\cos \Delta = \frac{R_e[R_p(\theta)^* g \cdot g'(\theta) \cdot (\overline{R}_s(\theta)^* \overline{g} \cdot \overline{g}'(\theta)](\theta_o)}{||R_p(\theta)^* g \cdot g'(\theta)|| \cdot ||R_s(\theta) g \cdot g'(\theta)||(\theta_o)} \qquad (5)$$

The formulas thus result from the previous formulas by replacing all the reflection coefficients by their convolution product with the function $9.9'(\theta)$.

For incoherent light and for a homogeneous sample the formulas will be:

$$\tan \psi = \left(\frac{||R_p(\theta)||^{2*}||g \cdot g'(\theta)||^2(\theta_o)}{||R_s(\theta)||^{2*}||g \cdot g'(\theta)||^2(\theta_o)}\right)^{\frac{1}{2}} \qquad (6)$$

$$\cos \Delta = \frac{R_e(R_p(\theta) \cdot \overline{R}_s(\theta)^* ||g \cdot g'(\theta)||^2)(\theta_o)}{(A \cdot B)^{\frac{1}{2}}} \qquad (7)$$

with $$A = ||R_p(\theta)||^{2*}||g \cdot g'(\theta)||^2(\theta_o)$$

$$B = ||R_s(\theta)||^{2*}||g \cdot g'(\theta)||^2(\theta_o)$$

It is noted that in the case of a plane wave $g = g' = 1$ for $\theta = \theta_o$ and O for $\theta \neq \theta_o$ and the formulas (4) and (6) on the one hand and (5) and (7) on the other hand can be reduced to the formulas (2) and (3).

Spectroscopic ellipsometry covers a wide spectral range leading to a focussing of the catadioptric type. In practice an optical system of spherical mirrors is used which are illuminated at an oblique incidence and thus have a considerable astigmatism. Because of this asigmatism the prior art solution, which simply consists of conjugating the monochromator slit and a point on the surface of the sample via the optical system is not suitable for forming a convergent image on the sample.

To remedy this inconvenience the optical illumination device according to the invention is characterized in that for realizing the said conjugation the device also comprises a second spherical mirror as well as an astigmatism correction slit arranged in the proximity of the image of the exit slit of the monochromator formed by the first spherical mirror and arranged perpendicularly to the exit slit and to the optical path so that said correction slit is conjugated with the sample through the second spherical mirror resulting in a luminous spot corrected for astigmatic errors being obtained on the surface of the sample.

In an advantageous embodiment permitting of deflecting the optical beam, a device as claimed in claim 1, characterized in that it comprises a first reflective mirror arranged in the optical path between the slit of the monochromator and the first spherical mirror, an a second reflective mirror arranged in the optical path between the second spherical mirror and the sample.

In a preferred embodiment the optical device is arranged in such a way that the luminous spot is a square whose side has a length of the order of 10 microns, and the angular aperture of the luminous beam is of the order of 4 to 5 degrees.

Figure 2:
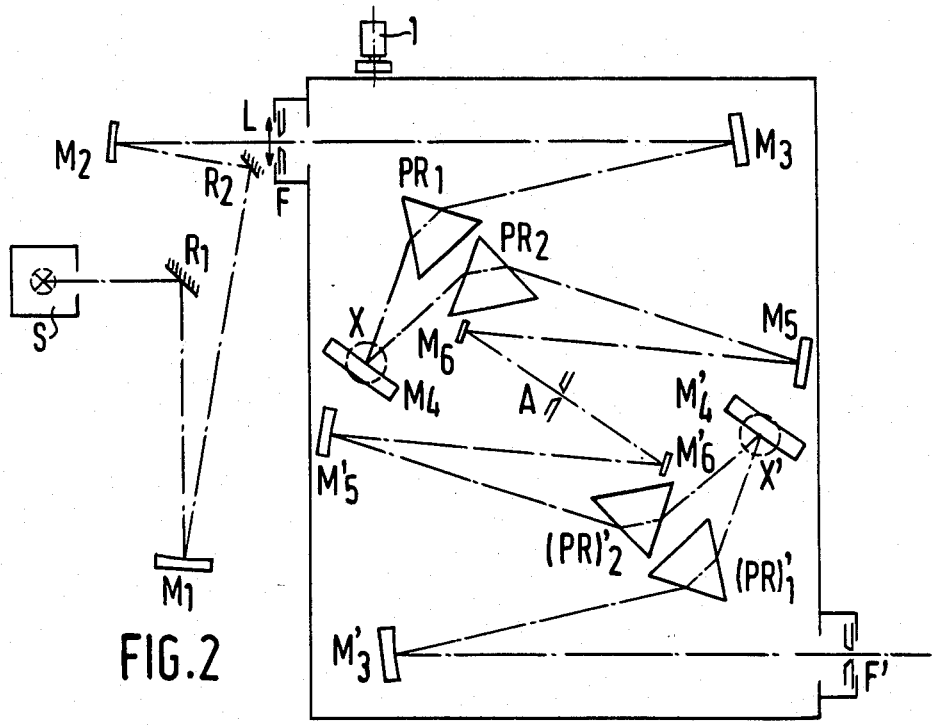
Figure 3:
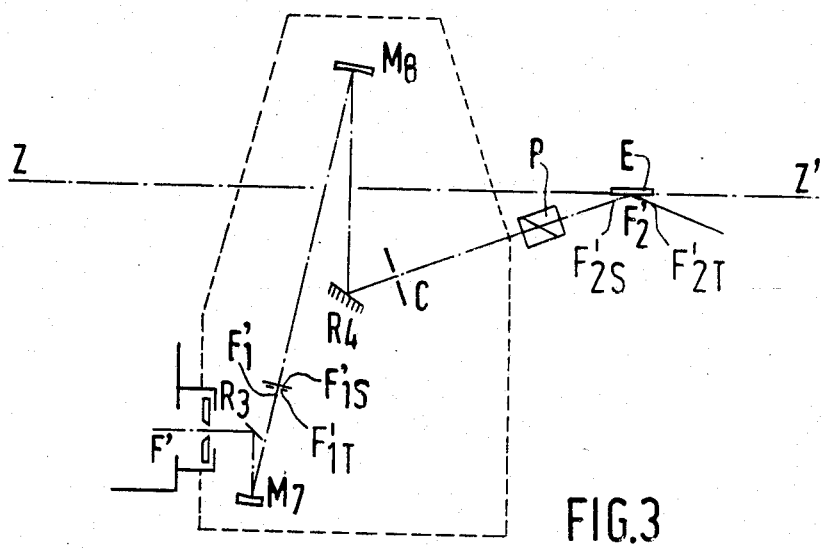
Figure 5:
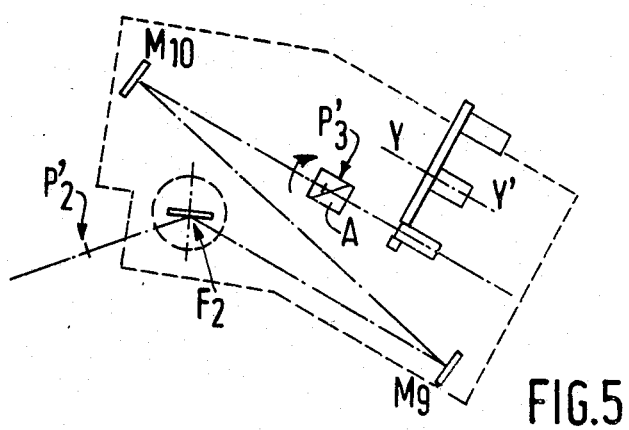
Figure 4:
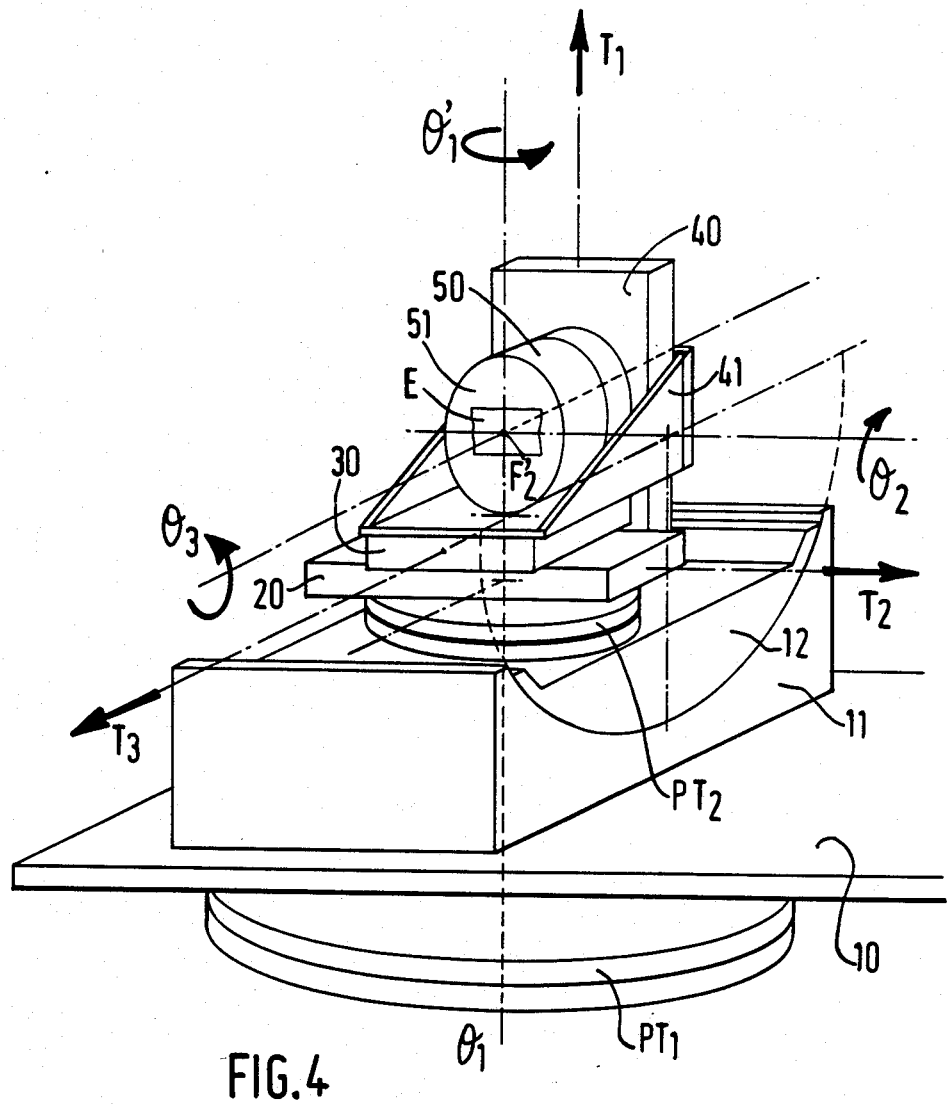

The invention will now be described in greater detail by way of example with reference to the accompanying drawings in which FIG. 1 shows the components of an incident field reflected on a plane surface, FIG. 2 shows a monochromator which can be used in an ellipsometer according to the invention, FIG. 3 shows an illumination arm according to the invention, FIG. 4 shows a sample support which can be used in an ellipsometer according to the invention and is suitable for cartographies, and FIG. 5 shows an analysis arm comprising the sample support and a detection system.

Ellipsometry is an optical characterization method which is usually used in the reflection mode and at an oblique incidence. In contrast to a reflectivity measurement it does not measure the absolute value of an intensity but determines a state of polarization of the light. The response of the gas chosen is different dependent on whether the electric field vector of the incident wave is parallel or orthogonal to the plane of incidence.

A plane wave having a polarization $E'_p$ which is parallel to the plane of incidence and forms an angle $\theta_o$ with the normal on the surface of the sample (FIG. 1) is reflected in the form of a wave having a polarization $E''_p$ which is submitted to a rotation of $\delta_p$ with respect to the incident wave. Similarly, a plane wave having a polarization $E'_s$ which is perpendicular to the plane of incidence is reflected in the form of a wave having a polarization $E''_s$ which is submitted to a rotation $\delta_s$ with respect to the incident wave.

The coefficients $R_p$ and $R_s$, see formula (1) are defined by the ratios:

$$R_p = \frac{E''_p}{E'_p} = |R_p|e^{i\delta_p}$$

$$R_s = \frac{E''_s}{E'_s} = |R_s|e^{i\delta_s}$$

As the coefficients for a homogeneous sample are Fresnel coefficients, the result is that $\rho$ is a function of the angle of incidence as well as of the optical properties of the sample and thus of the wavelength. In the case of a non-homogeneous sample, which may have a laminated structure, $\rho$ is a function of the optical properties of each layer and their thicknesses. In the case of a spatially non-homogeneous sample $\rho$ is also a function of the lateral coordinates of the sample. These considerations show that the number of unknown parameters may rapidly become quite considerable.

Generally an ellipsometric measurement at a fixed wavelength does not permit an adequately precise analysis of the sample. It is thus interesting to use another parameter and in the special case it is the wavelength. Thus a spectroscopic ellipsometry is concerned.

FIG. 2 shows a monochromator with prisms having a high spectral resolution which are particulary suitable for the envisaged application. It includes a 900 W Xenon lamp as a luminous source S. Such a lamp has not only a good stability but also a continuous intensity in a large spectrum ranging from infrared (several microns) to ultraviolet (approximately 0.22 micron).

The entrance slit F of the monochromator is illuminated by an optical system of the KOHLER type. This system permits of obtaining a uniform illumination. It comprises two spherical mirrors $M_1$ and $M_2$. The first mirror $M_1$ projects the image of the arc of the source S on the mirror $M_2$. The latter mirror conjugates the mirror $M_1$ on the entrance slit F of the monochromator. Two plane mirrors $R_1$ and $R_2$ maintain a small angle of incidence (approximately 5°) on the spherical mirrors $M_1$ and $M_2$. A lens L facing the entrance slit F is used for projecting the image of the arc formed on the mirror $M_2$ approximately to infinity in the monochromator.

The dispersive elements used are constituted by four double prisms of natural quartz $PR_1$, $PR_2$, $PR'_2$, $PR'_1$. This system is equivalent to two simple monochromators ($PR_1$, $PR_2$) and ($PR'_1$, $PR'_2$) arranged symmetrically with respect to a central slit A. Concave mirrors $M_3$ upstream of the prism $PR_1$ and $M_5$ downstream of the prism $PR_2$ for the first simple monochromator and $M'_5$ upstream of the prism $PR'_2$ and $M'_3$ downstream of the prism $PR'_1$ for the second simple monochromator constitute two systems at Z with equal angles of incidence. The system permits of conjugating the entrance slit F, the central slit A and the exit slit F'. The wavelength is selected by means of two plane mirrors $M_4$ arranged downstream of the prism $PR_1$ and upstream of the prism $PR_2$ and $M'_4$ arranged downstream of the prism $PR'_2$ and upstream of the prism $PR'_1$. A stepper motor 1 causes the mirrors $M_4$ and $M'_4$ to rotate simultaneously by means of a reduction gear unit. The stepper motor 1 is controlled by a computer in accordance with a precision calibration law permitting of linearly controlling the wavelength.

FIG. 3 shows the optical illumination arm whose function according to the invention is to form a spot of small dimensions, for example of the order of 10 microns, on the surface of the sample. Since the ellipsometer is of the spectroscopic type, a device with spherical mirrors is used. As the spherical mirrors are used at an oblique incidence, they have a considerable astigmatism. The sagittal and tangential focal lengths are different. If an optical assembly is used which simply conjugates the exit slit F' of the monochromator and a point $F'_2$ of the surface of the sample, an image is obtained which is not focussed due to the astigmatism of the spherical mirrors. The astigmatism effects are corrected in accordance with FIG. 3. In this Figure two spherical mirrors $M_7$ and $M_8$ are used, the mirror $M_7$ forming two images between $F'_{1T}$ and $F'_{1S}$ of the exit slit F' of the monochromator. The image $F'_{1S}$ is recaptured by the second adjustable mirror $M_8$ which conjugates the image in two images $F'_{2S}$ and $F'_{2T}$ upstream and downstream of $F'_2$ and in the immediate vicinity of $F'_2$ with the surface of the sample. A second slit is situated in the plane of $F'_{1S}$ and is arranged perpendicularly thereto.

The astigmatism effects can be corrected by means of the controlled distance between the two afore-mentioned slits. Reflective plane mirrors $R_3$ and $R_4$ deflect the beam. The assembly is made more compact, inter alia, by choosing focal lengths for the mirrors $M_7$ and $M_8$ such that the optical system works with a magnification 2, which provides the possibility of arranging the fixed polarizer P at a suitable distance from the sample for which the part of the luminous beam corresponds to that of the polarizer P.

The fixed polarizer P is made of calcite and is integral with a calibration control unit constituted by a stepper motor by means of which the polarizer P can be oriented in advance to a measurement with a precision of one hundredth degree. The assembly also includes an electronic shutter C arranged between the reflective mirror $R_4$ and the polarizer P. In the closed position of the shutter C the continuous component can be subtracted from the ellipsometric signal, for example the component caused by the dark current of the detector.

According to FIG. 4 the support for the sample has two degrees of freedom of rotation about the axes $\theta_1$, $\theta_2$ and preferably a third degree of freedom about the axis $\theta_3$ and three degrees of freedom of translation in accordance with the axes $T_1$, $T_2$ and $T_3$.

The first degree of freedom of rotation is obtained by means of two coaxial rotary movements. The first rotary movement about the axis $\theta_1$ which passes through the focal point $F'_2$ is ensured by a small rotary plate $PT_1$ controlled by a micrometer screw not shown. The small plate $PT_1$ is integral with a plate 10 which supports both the support for the sample and the analyzing arm which will be described hereinafter (FIG. 6). The rotation of the small plate $PT_1$ makes it possible to choose the angle of incidence in a manner as described hereinafter.

A second small rotary plate $PT_2$ rotating about the axis $\theta'_1$ coinciding with the axis $\theta_1$ in the adjusting position makes it possible to orient the sample without changing the angle of incidence determined by the position of the first plate $PT_1$.

The second rotation about a horizontal axis $\theta_2$ is obtained with a precision of one hundredth degree by displacing a goniometric cradle 12 rotating in a support 11 mounted on the plate 10. The axis $\theta_2$ intersects the axis $\theta_1$ at the focal point $F'_2$. As a result the axis $\theta'_1$ always passes through the focal point $F'_2$.

The goniometric cradle 11 carries the second small plate $PT_2$ which in its turn carries the rest of the apparatus ensuring the three translations in accordance with the axes $T_1$, $T_2$, $T_3$ and the rotation about the axis $\theta_3$. The translation according to the axis $T_2$ parallel to the axis $\theta_2$ is ensured by a plate 20 mounted on the rotary plate $PT_2$. The translation according to the axis $T_3$ perpendicular to the axis $T_2$ and to the axis $\theta'_1$ is ensured by a plate 30 mounted on the plate 20. Finally, the translation according to axis $T_1$ parallel to the axis $\theta'_1$ is ensured by a plate 40 mounted on the plate 30 by means of a bracket 41 and carrying a rotary plate 50 with the axis $\theta_3$ parallel to the axis $T_3$. The sample is fixed on the front face 51 of the rotary plate 50 with which the sample can be rotated about its own axis. The sample can thereby be given a desired orientation in preferred directions (metallisation lines, etc.).

The translations $T_1$ and $T_2$ ensured by the stepper motors with an increment of 0.1 micron provide the possibility of realizing a cartographic representation of the sample once the surface of the sample is made to coincide with the focal point $F'_2$ by acting on the translation $T_3$. The translations $T_1$ and $T_2$ do not eliminate the setting. Since the axes $\theta'_1$, $\theta_2$ pass through the focal point $F'_2$, the point on the surface of the sample which coincides with $F'_2$ does not change irrespective of the adjustment of the three rotations $\theta'_1$ and $\theta_2$.

According to FIG. 5 the analysing arm which is integral with the movable plate can pivot in its plane around the axis $\theta_1$ (plate $PT_1$) which provides the possibility of modifying the angle of incidence and can also give the ellipsometer the "straight line" configuration in which there is no reflection on the sample. This makes it possible to align the assembly of the optical system as well as taking the reference for the measurement of the angle of incidence. The analyzing arm comprises the sample support as well as a detection system including an optical detection system which comprises two spherical mirrors $M_9$ and $M_{10}$ of identical focus, mounted at Z, a rotating analyzer and a turret provided with different detectors, an alignment laser and a sighting microscope.

The mirror $M_9$ picks up the luminous beam reflected by the sample and reflects it on the mirror $M_{10}$ for focussing on the detectors of the turret after passing through the rotating analyzer A. The angle of incidence on the mirrors $M_9$ and $M_{10}$ is also chosen to be as small as possible, more specifically about 6 degrees, so as not to disturb the polarization of the reflected light.

The rotating analyzer A is made of calcite and is mounted in the hollow branch of a direct current motor. An optical coder is integral with the axis of the motor.

The turret is rotatable about an axis YY' so that the different detectors supported by this turret can be placed in the optical path and it covers different spectral ranges similarly as the alignment laser and the sighting microscope. The detectors are recessed to some extent from the focal plane so that a uniform illumination of each detector is ensured with the possible exception of detectors whose sensitive surface has small dimensions and which can be arranged in the focal plane.

The sighting microscope having a small magnification permits of observing the sample through the optical analysis system as well as the adjustment of the position of the mirror $M_8$ and of the slit $F'_1S$ of the optical illumination arm.

The alignment laser, which is a He-Ne laser in this case, permits of aligning the optical assembly comprising the sample support.

The signal I provided by the detector is sinus-oidal at a frequency which is twice that of the rotating analyzer. If A designates the angle of the rotating analyzer with respect to the axis p and P designates the angle of the polarizer with respect to the axis p, it holds that:

$$I = k(1 + \alpha_0 \cos 2A + \beta_0 \sin 2A)$$

with $$\alpha_0 = \frac{\tan^2\psi - \tan^2 P}{\tan^2\psi + \tan^2 P}$$

$$\beta_0 = \frac{2\tan\psi \tan P \cos\Delta}{\tan^2\psi + \tan^2 P}$$

in which $\alpha_o$ and $\beta_o$ are the normalized Fourier coefficients. The result is:

$$\tan\psi = \tan P \left( \frac{1 + \alpha_0}{1 - \alpha_0} \right)^{\frac{1}{2}}$$

-continued
$$\cos\Delta = \frac{\beta_0}{(1-\alpha^2 0)^{\frac{1}{2}}}$$

The latter two equations show that the ellipsometric measurements may be summarized to some extent measurements of the angles. In order that the measures have a good absolute precision it is important that all angles, namely the angle of incidence, the orientation of the polarizer and the marking of the position of the rotating analyzer are correctly determined. The orientation of the sample is also important because it determines the plane of incidence.

A calibration procedure of the ellipsometer, the analyzer arm, and thus the sample support shown in a straight-line configuration will now be described. The first operation is to adjust the position of the mirror $M_8$ and of the slit $F'_1S$ of the optical illumination arm with the aid of the sighting microscope. In the absence of the sample the beam of the laser arranged on the turret directly passes through the optical system in the inverse trajectory without being reflected. The position of the analyzing arm marked by the rotating plate $PT_1$ for which the laser beam passes through the centre of all the mirrors is taken as a reference for measuring the angle of incidence. With the optical axis thus being realized for the laser beam, one acts on the rotations in accordance with the axes $\theta'_1$ and $\theta_2$ of the sample support in such a way that a perfect parallelism is obtained between the surface of the sample and the laser beam, that is to say the condition of grazing incidence. Subequently one acts on the translation along the axis $T_3$ so that half the laser beam is shut off. This causes the focal point $F'_2$ of the illumination arm to coincide with a point on the surface of the sample. As an action on the rotations in accordance with the axes $\theta'_1$, $\theta_2$, $\theta_3$ (similarly as an action on the translation $T_1$ and $T_2$) does not change the position of the sample along the axis $T_3$, the adjustment can still be improved once the setting is realized.

After these adjustments the analyzing arm can be rotated and set to the measurement position. As the rotation of the small plate $PT_1$ is measured with a precision of one hundredth degree, the angle of incidence is thus precisely determined.

A perfect orientation of the surface of the sample can preferably be obtained by considering the signal detected by giving the assembly the measurement configuration. The rotating analyzer is brought to rotation at an angular frequency $\omega$. The detected signal has a frequency at a period of $2\omega$. An incorrect position of the sample with respect to the plane of incidence causes periodical terms of the frequency $\omega$ to appear in the signal. The alignment of the sample is thus realized by acting on the rotations $\theta'_1$ and $\theta_2$ so that the parasitic component of the frequency $\omega$ is eliminated. The visual examination of the signal on an oscilloscope by superposing two periods of the signal of the frequency $2\omega$ makes it possible to show all components of the frequency $\omega$.

The remaining degrees of freedom ($\theta_3$, $T_1$, $T_2$) no longer change the orientation of the plane of the sample. They provide the possibility of choosing the point to be measured on the sample (translation $T_1$ and $T_2$) and to realize cartographic representations thereof and in the case of a sample showing motives it is possible to align the latter (rotation $\theta_3$) parallel to a given direction, for example the horizontal or vertical direction.

The function of the degrees of freedom of the sample support can thus be summarized as follows:
the angle of incidence can be adjusted by means of the rotation $\theta_1$
the sample can be oriented with respect to the optical path by means of the rotations $\theta'_1$ and $\theta_2$ by rotating the sample in two orthogonal planes about the focal point $F'_2$.
the sample can be rotated by means of the rotation $\theta_3$ in its own plane about the axis passing through the focal point $F'_2$.
the translations $T_1$ and $T_2$ ensure the choice of the point on the sample which is to be measured.
the translation $T_3$ provides the possibility of bringing the sample in the plane of the focal point $F'_2$ whilst the thicknesses of the different samples can be taken into account.

Once the sample is positioned, the angular positions of the polarizer and the analyzer are to be marked. This can be done by minimizing the residual R defined by:

$$R = 1 - \eta^2(\alpha^2 + \beta^2)$$

in which $\eta^2$ is an attenuation coefficient produced by the electronic detection system filtering the signal supplied by the detector.

For measuring the residual the polarizer is manually positioned in the vicinity of the position p, namely at $p_o$. The value of the residual and the phase of the signal is measured at $2N+1$ equidistant points in the interval $p_o - \Delta p_o$, $p_o + \Delta p_o$. The variation of the residual around its minimum is approximated by a parabolic function whose coefficients are calculated by means of the smallest quadrant method.

This procedure makes it possible to position the polarizer with a precision of the order of two hundredths of a degree and to determine all the necessary parameters for deriving the Fourier coefficients corrected for the attenuation and phase difference from the measured Fourrier coefficients.

The attenuation $\eta^2$ is derived from the minimum value of $R = 1 - \eta^2$. This value depends on the time constant of the amplifier and the passband of the detector. For a photomultiplier, in which the passband is very large with regard to the modulation frequency, a time constant of 0.1 ms and a rotation frequency of 20 Hz for the rotating analyzer, the minimum value of R should be approximately 0.004.

For measuring the phase difference the value of $\alpha$ and $\beta$ should be 1 and 0, respectively, when the polarizer is in the position p=0. The measurement of the Fourier coefficients $\alpha'$ and $\beta'$ for p=0 give the value of the phase difference $\alpha$:

$$\tan\phi = \frac{\alpha'}{\beta'}$$

To carry out the measurements the polarizer is offset through an angle given by the position p=0 which is determined in the calibration phase.

What is claimed is:

1. An optical sample illumination device for a spectroscopic ellipsometer of the rotating analyzer type, comprising a monochromator having an exit slit whose image is conjugated with a surface of the sample by at least a first spherical mirror, and comprising a polarizer arranged between said spherical mirror and the sample, characterized in that for realizing the said conjugation the device also comprises a second spherical mirror as well as an astigmatism correction slit arranged in the proximity of the image of the exit slit of the monochromator formed by the first spherical mirror and arranged perpendicularly to the exit slit and to the optical path so that said correction slit is conjugated with the sample through the second spherical mirror resulting in a luminous spot corrected for astigmatic errors being obtained on the surface of the sample.

2. A device as claimed in claim 1, characterized in that it comprises a first reflective mirror arranged in the optical path between the slit of the monochromator and the first spherical mirror, an a second reflective mirror arranged in the optical path between the second spherical mirror and the sample.

* * * * *